(12) United States Patent
Bentz

(10) Patent No.: US 11,878,007 B1
(45) Date of Patent: Jan. 23, 2024

(54) METABOLISM ENHANCING COMPOSITIONS

(71) Applicant: Red Mountain Red Spa, LLC, Scottsdale, AZ (US)

(72) Inventor: Suzanne Bentz, Scottsdale, AZ (US)

(73) Assignee: RED MOUNTAIN MED SPA, LLC, Scottsdale, AZ (US)

( * ) Notice: Subject to any disclaimer, the term of this patent is extended or adjusted under 35 U.S.C. 154(b) by 0 days.

(21) Appl. No.: 17/818,836

(22) Filed: Aug. 10, 2022

(51) Int. Cl.
| | |
|---|---|
| *A61K 31/4375* | (2006.01) |
| *A61K 45/06* | (2006.01) |
| *A61K 31/05* | (2006.01) |
| *A61K 31/01* | (2006.01) |

(52) U.S. Cl.
CPC .......... *A61K 31/4375* (2013.01); *A61K 31/01* (2013.01); *A61K 31/05* (2013.01); *A61K 45/06* (2013.01)

(58) Field of Classification Search
CPC ................................................ A61K 31/4375
See application file for complete search history.

(56) References Cited

U.S. PATENT DOCUMENTS

| | | | |
|---|---|---|---|
| 6,277,396 B1 * | 8/2001 | Dente ............ | C08G 63/82 424/439 |
| 6,818,234 B1 * | 11/2004 | Nair ............... | A61K 36/29 424/732 |
| 2004/0077080 A1 * | 4/2004 | Raucy ............. | C12Q 1/48 435/325 |
| 2005/0100622 A1 * | 5/2005 | Nair ............... | A61K 36/29 514/456 |

* cited by examiner

*Primary Examiner* — Yong S. Chong
(74) *Attorney, Agent, or Firm* — Snell & Wilmer L.L.P.

(57) ABSTRACT

In various embodiments of the present disclosure, compositions exhibiting metabolism boosting effect are described. In various examples, compositions comprise a synergistic combination of at least one plant, root, seed, or fruit material, or extract thereof, or bioactive therefrom; at least one vitamin, essential trace mineral, or enzyme or vitamin cofactor; at least one amino acid; and at least one antioxidant. In various aspects, metabolism enhancing compositions are formulated as loose powders filled into capsules as orally administered dietary supplements. In various embodiments, compositions of the present disclosure are used to treat metabolic syndrome in subjects expressing symptoms thereof.

4 Claims, No Drawings

METABOLISM ENHANCING COMPOSITIONS

FIELD

The present disclosure generally relates to dietary supplements and more specifically to pharmaceutical compositions capable of stimulating and boosting metabolism through cellular activation of 5' AMP-activated protein kinase.

BACKGROUND

Metabolic syndrome is a chronic condition brought on by any number of factors such as poor eating habits, lack of physical exercise, smoking, excessive alcohol consumption, and stress. Everyday persons not familiar with medical terminology might feel they have a sluggish gut, poor digestion and are fatigued. There are at least three million cases of metabolic syndrome per year in the U.S. The ramifications of slow metabolism include high blood pressure, high blood sugar, insulin resistance, excess body fat around the waistline or abdomen leading to the classic apple or pear shapes, abnormal cholesterol levels, and increased risk for heart attack and stroke.

A slow metabolism can be enhanced or boosted by several remedial actions, including lifestyle changes, like exercise and smoking cessation, and changes in diet, such as consuming probiotics and taking various medications and supplements.

What is still needed is a non-prescription supplement having synergistic botanical and vitamin ingredients capable of boosting metabolism and assisting an individual in need thereof in mitigating the deleterious effects of metabolic syndrome in a simple manner.

SUMMARY

In accordance with various embodiments of the present disclosure, a metabolism boosting composition is described. The metabolism boosting composition comprises:
(1) at least one plant, root, seed, or fruit material, or a corresponding extract thereof, or corresponding bioactive therefrom;
(2) at least one vitamin, essential trace mineral, or enzyme or vitamin cofactor;
(3) at least one amino acid;
(4) at least one antioxidant; and
(5) optionally, an excipient.

In various examples, the metabolism boosting composition is compounded as a loose dry powder and filled into approximately 500 mg capsules for convenient daily oral administration.

DETAILED DESCRIPTION

While these exemplary embodiments are described in sufficient detail to enable those skilled in the art to practice the invention, other embodiments may be realized and that logical, chemical, and mechanical changes may be made without departing from the spirit and scope of the inventions. Thus, the detailed description is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments of the present disclosure, a composition for boosting metabolism in a human or non-human animal is disclosed. In various aspects, a composition in accordance with the present disclosure comprises:
(1) at least one plant, root, seed, or fruit material, or a corresponding extract thereof, or corresponding bioactive therefrom;
(2) at least one vitamin, essential trace mineral, or enzyme or vitamin cofactor;
(3) at least one amino acid;
(4) at least one antioxidant; and
(5) optionally, an excipient.

As detailed below, ingredients in each of the above-delineated constituent groups have synergy of purpose in that certain combinations activate different biochemical pathways that improve insulin and leptin sensitivity, activate 5'-AMP-activated protein kinase, decrease cellular inflammation, increase mitochondrial activity, and activate brown adipose tissue and the glucose pyruvate ATP pathway to create energy from food. The synergistic mixtures discovered that provide these unexpected pharmacological effects are mixtures of:
(a) *Gynostemma pentaphyllum* (Jiaogulan) leaves and stem extract, *Kaempferia parviflora* root extract, *Garcinia mangostana* fruit extract, *Laminaria japonica* fucoxanthin extract of whole kelp, and berberine HCl, together in combination with:
(b) chromium, Vitamin B7, vanadium, zinc, Vitamin C, L-tyrosine and L-cysteine.

This unique combination of (a) and (b) above activate 5'-adenosine monophosphate-activated protein kinase (or AMPK). AMPK is an enzyme that plays a part in cellular energy homeostasis, largely to activate glucose and fatty acid uptake and oxidation when cellular energy is low. AMPK activation is known to stimulate hepatic fatty acid oxidation, ketogenesis, skeletal muscle fatty acid oxidation and glucose uptake, inhibit cholesterol synthesis, lipogenesis, and triglyceride synthesis, inhibit adipocyte lipogenesis, adipocyte lipolysis, and modulate insulin secretion from pancreatic β-cells. At least in part, the metabolism boosting compositions of the present disclosure activate AMPK. Thus, through this net effect, the metabolism boosting compositions of the present disclosure find use in the treatment of metabolic syndrome.

Besides activation of AMPK, the metabolism boosting compositions of the present disclosure increase mitochondria activity and ATP, leading to improved glucose utilization and increased fat metabolism. Thus, through these effects, the metabolism boosting compositions of the present disclosure find use in the treatment of metabolic syndrome.

Definitions and Interpretations

It should be noted that as best as the compounds and substances that make up a metabolism boosting composition herein are categorized for convenience, overlap in function is certain. An example is Vitamin C, which although characterizable as both a vitamin and an antioxidant, will be included within the scope of the limitation "at least one vitamin."

As used herein, the term "plant" takes on its ordinary meaning in biology, recognizing that this term includes terrestrial as well as aquatic plants—i.e., seaweed and kelp, along with epiphytic plants and lithophytes. Wherever possible, a distinction is made between parts of plants, such as the roots, leaves, stems, buds, seeds, fruits, and so forth. This distinction is straightforward in instances where plant "parts" are used directly in the compositions of the present disclosure (e.g., for example, the leaves of a plant, dried and powdered), or in the instances of extracts of plant leaves and stems or extracts of fruit surrounding seeds or extracts of bare seeds. An example is pomegranate (seed) extract (*Punica granatum*, seed), which can be the extract of the fruity material surrounding the hard seed. When extracting the "arils," (i.e., the juicy seeds of the pomegranate), the bright red juice becomes a major constituent of the aril extract, and that the hard inner seeds do not contribute botanicals to the extract unless they are ground prior to extraction. Extraction of bare ground seeds, for example, would be expected to contribute punicic acid, Vitamin E, magnesium, and various tannins and lignin to the extract composition.

As used herein, the term "extract" refers generally to a liquid composition (or a powdered composition upon solvent evaporation from a liquid) containing biological materials (natural products) obtained by exposing plant (leaves, stems, flowers, buds, etc.), root, seed or fruit materials to various solvents, such as water and/or alcohol or other suitable solvents, under various conditions (e.g. heating or ambient), for various lengths of time (seconds, minutes, days, weeks, months, etc.). Extracts may be filtered to remove solids, decanted, diluted, or used as is. In many examples, such a liquid solvent extract is evaporated to dryness (such as under vacuum, or freeze-dried) to produce a powdered extract. It some instances, the biological materials in an extract may be identified and known (e.g., an alkaloid, flavonoid, etc.), but it should be appreciated that for many plant extracts, the mixture of biological materials present in the extract may be quite complex and perhaps not fully characterizable. An extract herein is an identifiable substance and should not be considered indefinite based on what might be a complex and uncharacterizable mixture of constituents. An extract herein will typically be described by its manufacturing process, such as for example, ethanol extract of macerated plant leaves and stems. For example, an ethanol extract may be prepared from a particular fruit material and alcohol (ethanol), whereby 1 part by weight botanical substance is combined with 9 parts by weight alcohol in a Soxhlet extractor.

As used herein, the term "amino acid" takes on its ordinary meaning in the chemical and biochemical arts, meaning a compound having both amine and carboxylic acid functionality. A subgroup of amino acids recognized as α-amino acids have the α-positioning between the amine and carboxylic acid functionality. For use herein, an amino acid includes one or more natural, synthetic, semi-synthetic, common, uncommon, known, or unknown amino acids, in any combination, wherein the one or more amino acids comprise any juxtaposition of the —NH$_2$ (or secondary or tertiary amine) and —CO$_2$H substituents, (e.g., α-, β-, γ-, δ-, etc.). In various embodiments, at least one α-amino acid is included in the metabolism enhancing composition. TABLE 1 lists the twenty common α-amino acids that, individually or in combination, find use in the compositions of the present disclosure. Typically, the naturally occurring enantiomer (L-) is of importance for use in dietary supplements, recognizing that glycine has no chirality.

TABLE 1

Common α-Amino Acids

| Amino Acid | Abbreviation | Formula (molecular weight) |
|---|---|---|
| Alanine | Ala | $C_3H_7NO_2$ (89.09) |
| Arginine | Arg | $C_6H_{14}N_4O_2$ (174.20) |
| Asparagine | Asn | $C_4H_8N_2O_3$ (132.12) |
| Aspartic Acid | Asp | $C_4H_7NO_4$ (133.10) |
| Cysteine | Cys | $C_3H_7NO_2S$ (240.30) |
| Glutamic Acid | Glu | $C_5H_9NO_4$ (147.13) |
| Glutamine | Gln | $C_5H_{10}N_2O_3$ (146.15) |
| Glycine | Gly | $C_2H_5O_2$ (75.07) |
| Histidine | His | $C_6H_9N_3O_2$ (155.16) |
| Isoleucine | Ile | $C_6H_{13}NO_2$ (131.18) |
| Leucine | Leu | $C_6H_{13}NO_2$ (131.18) |
| Lysine | Lys | $C_6H_{14}N_2O_2$ (146.19) |
| Methionine | Met | $C_5H_{11}NO_2S$ (149.21) |
| Phenylalanine | Phe | $C_9H_{11}NO_2$ (165.19) |
| Proline | Pro | $C_5H_9NO_2$ (115.13) |
| Serine | Ser | $C_3H_7NO_3$ (105.19) |
| Threonine | Thr | $C_4H_9NO_3$ (119.12) |
| Tryptophan | Trp | $C_{11}H_{10}N_2O_2$ (204.23) |
| Tyrosine | Tyr | $C_9H_{11}NO_3$ (181.19) |
| Valine | Val | $C_5H_{11}NO_2$ (117.15) |

As used herein, the term excipient is used broadly to include non-functional filler and functional, but perhaps non-nutritional materials. In various embodiments, filler may be added in quantity sufficient to complete a formula to "1000%" total. In various embodiments, metabolism enhancing compositions may comprise several pharmacologically active substances, such as botanical extracts, vitamins, minerals, enzymes, cofactors, bioflavonoids, and so forth, with the remainder comprising inert filler. Fillers increase weight, but typically do not contribute much if any pharmacological effect. Pharmaceutically acceptable inert fillers are known to the pharmaceutical arts, and include such substances as carbonates (e.g., calcium carbonate), phosphates (e.g., calcium phosphate), silica and silicates, and sulfates (e.g., calcium sulfate). For an exhaustive listing of pharmaceutically acceptable fillers, see "Handbook of Pharmaceutical Excipients, 6$^{th}$ Edition, R. C Rowe, et al., editors, Pharmaceutical Press, London, 2009. The term excipient also refers to additional functional ingredients in a metabolism enhancing composition, and thus can be functionally distinguishable from inert filler per se. Excipient refers to those ingredients that although functional, play a minor role in the composition, and little if any nutritional value. These ingredients typically include leveling agents, blending aids (e.g., stearates), emulsifiers, disintegrants, anticaking agents, colors, flavors, sweeteners, and preservatives. Examples include, but are not limited to, monosaccharides and disaccharides, (e.g., mannitol, lactose, dextrose), polysaccharides, starch, and starch derivatives (e.g., various flours like rice flour, mesquite flour), pigments, food coloring, mint, aspartame, and so forth. In various embodiments, the amount of filler in a composition herein that is formulated into a capsule for oral consumption may be substantial, such as for example, between about 25 wt. % to about 30 wt. % of the total weight of the contents of an orally administered capsule, less capsule weight.

As used herein, the term "composition" takes on the ordinary meaning in formulation chemistry as a combination of ingredients. In various embodiments, a composition is designed to adopt a particular physical form, or at least be amenable to physical change into a desired physical form, which may be the dosage form for a particular treatment regimen. Typically, a composition is made homogeneous by mixing or blending, although not all liquid compositions are colorless and transparent and not all powder compositions are white and perfectly finely granular. Compositions comprising an emulsion, dispersion or suspension may be homogeneous because the droplets or particles are evenly spread in a carrier. So, for example, a composition herein may be in the form of a thin liquid (having a viscosity at or near that of water), a viscous liquid (having a liquid of viscosity greater than water), a paste, a cream, a jelly, a gel, or a powder. Ingredients for a composition herein are generally shown "as added," meaning there is a possibility for one or more chemical reactions between ingredients once the ingredients are mixed, such as into a common carrier. One skilled in the art of formulation chemistry can recognize whether ingredients might react in a mixture. These reactions can include neutralization (e.g., between acid and alkali ingredients), mixed micelle formation (mixed surfactants in liquid systems) or other encapsulation phenomena, hydrolysis, and so forth. In various embodiments, a composition herein comprises a blended powder that can be packed into capsules for oral administration. In some instances, a composition may take into consideration an outer encasing when that material is also included in the administration of the composition to an individual. For example, a gelatin capsule, or a cellulose capsule, may be included in the listing of ingredients for a composition, or perhaps just the ingredients of the contents of the capsule may be listed. In various embodiments, ingredients in a composition are listed in "weight percent," (i.e., "wt. %"), based on the total weight of the composition. For example, 100 milligrams of a composition comprising 40 mg A and 60 mg B may be recited as "40 wt. % A and 60 wt. % B, based on the total weight of the composition," which necessarily totals to "100 wt. %." The actual weight amounts, (e.g., milligrams or grams) generally refers to amounts added for a particular batch size, (e.g., a batch size of a loose blended powder usable to fill 100, 1000, 10,000, etc. individual capsules).

As used herein, the term "dosage form" takes on its ordinary meaning in the pharmaceutical arts as the physical form of a composition designed for a particular administration route. For example, dosage forms include, but are not limited to, injectables, infusible liquids, nasal sprays, nasal gels, topicals such as transdermal creams, ointments and patches, loose powders, tablets, sublingual tabs, capsules, lozenges, syrups, vapors, and so forth. In various embodiments, compositions of interest herein comprise loose blended powders, and the dosage form comprises a capsule comprising the powdered composition encased or "encapsulated" or "filled" in the capsule, or a table comprising the powdered composition compressed into a small shape for oral swallowing or sublingual dissolution.

As used herein, the term "capsule" generally refers to a one- or two-piece enclosure for containing a loose powder, which can be swallowed for oral administration of the powder contents of the capsule, or a soft-shell for a liquid composition (otherwise known as a "gel cap"). In general, "soft" capsules for liquids are one-piece, whereas "hard" capsules for powders are two-piece. In some instances, the capsule is said to "encapsulate" the powder contained therein, which can be confusing because the term "encapsulation" is often used, perhaps more correctly, to describe a microscale or nanoscale phenomenon rather than describing something macroscopic like a supplement dosage form. In various embodiments, capsules for use herein are hard, stable two-piece shells, or enclosures, capable of stably holding a powder fill, and capable of disintegrating in the gastrointestinal track of an individual. Capsules for use herein may comprise any combination of animal gelatin, plant polysaccharides (cellulose, carrageenan, etc.), or starch or derivatives thereof. In some instances, capsules may further comprise plasticizers, colors, preservatives, disintegrants, lubricants, and various surface treatments such as laser perforations. In various embodiments, a capsule may be transparent so that the contents are visible, or entirely opaque to obscure the contents. In various embodiments, the rate of delivery of a dietary supplement from a two-piece hard capsule having a powder fill may be controlled by any combination of ingredients in the powder fill and ingredients or design configurations of the capsule itself. For example, a capsule intended for immediate release of dietary supplements may comprise a micronized powder fill in combination with a laser perforated capsule having disintegrants incorporated in the capsule material. On the other hand, a capsule intended for slow or controlled release may have a powder fill configured with a controlled release agent, like a cellulosic, to coagulate in the gut, slowing active bioavailability of the constituents of the supplement, in combination with a slower dissolving capsule shell, such as one comprising a plasticizer. In various embodiments, one or more constituents of a metabolism boosting composition may be embedded in the capsule material itself.

Two-piece hard capsules for use herein can be characterized by a size scale that includes size 5, 4, 3, 2, 1, 0, 0E, 00, 000, 13, 12, 12el, 11, 10, 7 and Su07, (in increasing order of physical dimensions and internal volume when assembled). Typically, only the capsule sizes from 5 (11.1 mm×4.91 mm, 0.13 mL volume) up through about 000 (26.14 mm×9.91 mm, 1.36 mL) would be practical for human oral consumption, and digestive tract (enteral) route of administration.

As used herein, the term "subject" or the phrase "a subject in need thereof" refers to any human or non-human animal requiring, or desirous of, a pharmacological change. For example, a subject in need thereof may be a human patient clinically diagnosed with metabolic syndrome, fatigue, slow metabolism, sluggish gut, an eating disorder, or health issues relating to poor BMI, fat along the waistline, diet in general, or lack of exercise. In some instances, a subject in need thereof may be showing symptoms that either subjectively or objectively relate back to metabolism issues and possibly metabolic syndrome, such as abdominal obesity, high blood pressure, impaired fasting glucose, high triglycerides levels, low HDLK cholesterol levels, and so forth. In various embodiments, the subject in need thereof is a person desirous of a boosted metabolism and more energy overall, such that they can lose weight, experience better digestion and/or improve general health. Most importantly, a subject in need thereof can be any human in good health, but desirous of maintaining good health. In other words, the subject in need thereof may be desirous of a prophylactic regimen, like taking daily vitamins. The subject in need thereof may have the outward appearance of a person of average weight and vitality for their age, height, and gender, but desirous of maintaining that weight and figure, and thus desirous of maintaining a certain level of metabolism in general.

As used herein, the term "treatment" of a subject (e.g., a human) is any type of intervention used to alter the natural course of the subject. Treatment includes, but is not limited to, administration of a metabolism enhancing composition in accordance with the present disclosure and may be performed either prophylactically, or subsequent to, the initiation of a pathologic event or diagnosis of a physical issue, such as slow metabolism and fatigue or clinical metabolism syndrome. Also included are "prophylactic" treatments, which can be directed to reducing the rate of progression of obesity or condition relating to slow metabolism, delaying the onset of weight or condition, or reducing the severity of its onset. "Treatment" or "prophylaxis" does not necessarily indicate complete eradication, cure, or prevention of a disease or any condition, or associated symptoms thereof. Treatment may also be entirely for reasons not diagnosable or observable objectively by a medical practitioner, such as when an individual just simply feels fatigued and that their digestive system is "sluggish" in a nondescript way. In various embodiments, compositions herein find use in the manufacture of a medicament for treatment of metabolic syndrome.

As used herein, the term "therapeutically effective amount" refers to a minimum dosage of a composition in accordance with the present disclosure that provides a desired effect. Therefore, a therapeutically effective amount varies by subject, dosage form, concentration of the one or more vitamins and extracts in the composition, and the ultimate results desired. For example, a therapeutically effective amount of a capsule dosage form disclosed herein to boost metabolism and mitigate the feeling of a sluggish gut in an individual in need thereof might be on the order of four (4) 500 mg capsules per day (2 grams per day of metabolism boosting composition in total). In other examples, a therapeutically effective amount of a capsule disclosed herein to boost metabolism and mitigate the feeling of a sluggish gut in an individual is on the order of one (1) to eight (8) 500 mg capsules per day (0.5 to 4 grams per day of metabolism boosting composition in total).

As used herein, the term "prophylactically effective amount" refers to a minimum dosage of a metabolism boosting composition in accordance with the present disclosure that provides maintenance of a desired level of health. Therefore, a prophylactically effective amount varies by subject, (particularly age, gender, height, weight, and current health habits and any ongoing health issues), dosage form, concentration of one or more of the various vitamins and extracts in the composition, and the results desired. In various instances, a prophylactically effective amount of a composition disclosed herein in capsule dosage form to promote general health in a male or female human of average weight is on the order of one (1) to eight (8) 500 mg capsules per day (0.5 to 4 grams per day of metabolism boosting composition in total). In more specific examples, a prophylactically effective amount of a capsule composition disclosed herein to promote general health in a male or female human of average weight who exercises moderately and eats reasonably healthy food may be about four (4) 500 mg capsules per day, either at once at a particular time of the day or spaced apart with each meal or snack.

As used herein, the terms "boost," "ignite," enhance," and "stimulate," interchangeably mean to either increase or decrease one or more quantifiable parameters relating to metabolism in a human or non-human animal, optionally by a defined and/or statistically significant amount. "Boosting," "igniting," enhancing," and "stimulating," refer generally to the ability of one or more metabolism enhancing compositions in accordance with the present disclosure to produce or cause a greater physiological response (i.e., downstream effects) in a cell or in a subject relative to the response caused by either no metabolism enhancing composition or a control composition or placebo. Relevant physiological or cellular responses (in vivo or in vitro) upon administration of a metabolism enhancing composition to an individual in need thereof will be apparent to persons skilled in the art. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times), including all integers and decimal points in between and above 1 (e.g., 1.5, 1.6, 1.7. 1.8), the amount produced by no metabolism enhancing composition (the absence of various vitamins, extracts, and so forth) or a control compound. The term "reduce" or "inhibit" may relate generally to the ability of one or more metabolism enhancing compositions to "decrease" a relevant physiological or cellular response, such as a symptom of a disease like metabolic syndrome or a condition like fatigue or sluggish gut described herein, as measured according to routine techniques in the diagnostic art. Relevant physiological or cellular responses (in vivo or in vitro) will be apparent to persons skilled in the art, and may include reductions in the symptoms or pathology of a disease such as metabolic syndrome and related issues like fat accumulation in the liver and/or adipose tissues, incorrect/ineffective microbiota flora in the gut, abdominal obesity, high blood pressure, and insulin resistance. A "decrease" in a response may be "statistically significant" as compared to the response produced by no metabolism boosting composition or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

General Embodiments

In general, the present disclosure describes metabolism enhancing compositions comprising:
(1) at least one plant, root, seed, or fruit material, or extract thereof, or bioactive therefrom;
(2) at least one vitamin, essential trace mineral, or enzyme or vitamin cofactor;
(3) at least one amino acid;
(4) at least one antioxidant; and
(5) optionally, an excipient.

In various embodiments, a blend of plant, root, seed, and fruit materials and various extracts of various plant, root, seed, and fruit materials and bioactive substances is present in a metabolism boosting composition at from about 30 wt. % to about 50 wt. %, based on the total weight of the metabolism enhancing composition. For example, this "botanical" portion of a composition, as it may be referred, comprises 35 wt. % to 45 wt. %, 35 wt. % to 40 wt. %, or 35 wt. % to 37 wt. %, based on the total weight of the metabolism enhancing composition. The botanical portion of a metabolism boosting composition may be referred to as the "proprietary blend" for purposes of an ingredient statement placed on a package of supplements, for at least the reason that the exact identity and individual weight percentages of each bioactive substance may never be known. For example, some kelp extracts alone contain mixtures of complex marine polysaccharides that are difficult if not impossible to structurally elucidate, and a proprietary blend herein may contain many such extracts, each one uncharacterizable to some extent. The proprietary blend portion of a metabolism boosting composition may also include the antioxidant(s) and/or amino acid(s) components, such as if labeling rules require the vitamins and minerals to be separately delineated, leaving the remainder of the composition to be disclosed on the label as proprietary blend.

Options and combinations within the botanical portion of a metabolism boosting composition of the present disclosure are set forth in detail below:

Plant, Root, Seed, or Fruit Material, or Corresponding Extract Thereof or Bioactive Therefrom In various embodiments, compositions of the present disclosure comprise at least one plant, root, seed, or fruit material, or a corresponding extract of any of these materials, or a bioactive substance isolated from any of these materials, recognizing that the plant may be terrestrial or aquatic. Compositions of the present disclosure benefit from a combination of terrestrial and aquatic plant materials or their corresponding extracts.

In various embodiments, a composition for enhancing metabolism comprises at least one plant material used directly in the composition, such as the dried and powdered leaves and stems harvested from a particular plant. In other compositions, a composition for enhancing metabolism comprises at least one plant or root extract, or an extract of seeds or fruits of a plant.

Many terrestrial and aquatic plants of interest herein can be dried or otherwise desiccated, and then pulverized by any mechanical means into a powder for blending into a metabolism boosting composition. Many dried herbs and spices for cooking are produced in this way, and the same process can be used with plant material for use in a metabolism boosting composition. In various embodiments, a composition for enhancing metabolism comprises at least one extract of a plant, root, seed, or fruit material, wherein the plant (and source of roots, seeds, etc.) is terrestrial or aquatic. One example of a dried plant powder for use herein is dried and pulverized kelp, such as nori. In various examples, a plant, root, seed, or fruit material extract may be standardized to contain a particular level of a known bioactive substance. In some instances, an extract may be evaporated into a powdered extract. In various embodiments, a powdered extract is expected to be more nutrient rich than dried and macerated plant or root from which the extract was obtained. For example, non-dietary fibrous materials can be excluded by extraction of a plant with water or ethanol, and therefore not included in a powdered extract.

Terrestrial and aquatic plants of interest herein, usable directly as the actual plant, root, seed or fruit material when dried and powdered, or as extracts of terrestrial or aquatic plants, roots, seeds or fruits used as is (in liquid form with solvent, or evaporated into powdered extracts), include, but are not limited to, *Laminaria japonica, Alchemilla japonica, Undaria pinnatifida, Porphyra haitanensis, Ulva prolfera, Ascophyllum nodosum*, spinach, spearmint, pumpkin, psyllium, *Punica granatum*, peppermint, neem, apple, propolis, *Orthosiphon stamineus, Pygeum africanuum*, inulin, lion's mane, mustard, *Eleutherococcus, Agaricu blazei*, wheat grass, purslane, *Pterocarpus marsupium*, milk thistle, chaga, *Bacopa monnieri*, naringenin, magnolia, kudzu, hemp, cucubita, catauba, burdock, garlic, black garlic, *Gynostemma pentaphyllum*, β-cryptoanthin, angelica, *Alchemilla vulgaris, Agaricus bisporus*, yucca, Theobroma cacao, schisandra, beet, scutellaria, *Salvia miltiorrhiza*, reishi mushroom, oregano, maitake mushroom, *Curcuma zedoaria*, cinnamon, cardamon, bearberry, Baikal skullcap, *Aremisia annua, Kaempferia parviflora* (black ginger), *Zingiber officinale* (common ginger), *Panax ginseng, Eleutherococcus senticosus* (Siberian *ginseng*), *Panax quinquefolius* (American ginseng), *Brassica nigra, Eleutherococcus senticosus, Alchemilla japonica Nakai et Hara, Agaricus blazei, Thinopyrum intermedium, Prunus cerasu, Portulaca oleracea* L., *Vaccinium macrocarpon, Phaseolus vulgaris, Cinnamomum cassia, Elettaria caramomum, Arctostaphylos urva ursi, Scutellaria baicalensis, Garcinia mangostana, Hypericum perforatum* L., *Litsea cubeba, Carica papaya, Althaea offi-cinalis* L., *Lepidium meyenii, Cymbopogon citrates, Amorphophallus konjac, Camellia sinensis, Irvingia gabonensis, Haematococcus pluvialis, Oenothera speciosa, Cyanotis arachnoidea, Salvia miltiorrhiza Bunge, Chlorella vulgaris, Hordeum vulgare* L., *Urtica dioica* L., *Petroselinum crispum, Paullina cupana, Griffonia simplicifolia, Ginko biloba* L., and *Ocimum basilicum*. Various botanicals and extracts thereof for use herein may be obtained, for example, from Naturmed Scientific GMBH, Wiesbaden, Germany or Naturmed Scientific PVT LTD, Delhi, India In various embodiments, a composition for enhancing metabolism comprises at least one fruit powder. Fruit powders for use herein include, but are not limited to, raspberry, date, fig, evaporated grape juice, evaporated lemon juice, mango, evaporated orange juice, evaporated papaya juice, evaporated pineapple juice, strawberry, tamarind, watermelon, blackberry, blueberry, apple, pomegranate, acai, lychee, rambutan, durian, langsat, jackfruit, star apple, cherimoya, salak, passion fruit, breadfruit, papaya, pomelo, cheery, santol, and mangosteen. In various embodiments, a fruit powder may be obtained by dehydrating fruit and milling the dried material into a powder. Alternatively, a fruit juice may be evaporated or otherwise dried into a fruit powder. Any process known by one of skill in the art of botanical preparations may be used to obtain a fruit powder from fruit or fruit juice. Various fruit powders from fruits or juices for use herein may be obtained, for example, from Naturmed Scientific GMBH, Wiesbaden, Germany or Naturmed Scientific PVT LTD, Delhi, India.

In various embodiments, a metabolism boosting composition comprises dried and powdered *Garcinia mangostana* (mangosteen) fruit. This fruit powder is rich in the polyphenolic xanthone α-mangostin. *Garcinia mangostana* dried fruit powder is available, for example, from Kalustyan's, New York, NY.

In various embodiments, a metabolism boosting composition comprises a *Punica granatum* extract, such as a fruit rind extract, a juice powder, or a seed extract. Pomegranate seeds are rich in conjugated fatty acids, with the total lipid content varying between 7.9% and 16% by weight. Pomegranate seed oil consists of 65%-85% conjugated fatty acids, the most abundant of which are the 9-cis, 11-trans, and 13-cis-octadecatrienoic acid, or punicic acid—a conjugated linolenic acid. Pomegranate seed oil, which is rich in tocopherols, has a majority of γ-tocopherol. The total tocotrienol (α- and β-tocotrienol) content is between 1.7% and 4.8% of total tocols. Pomegranate seed oil also contains bioactive lipids, such as phytosterols, phospholipids, and triterpenes. Since pomegranate fruit contains many phenolics, pomegranate seed oil has biological properties. *Punica granatum* seed extract, CAS No. 84961-57-9, is available, for example, from AuNutra Industries, Inc., Chino, California 91710.

In various embodiments, aquatic plant materials for use herein include, but are not limited to, various seaweeds and kelp such as *Laminaria japonica, Alchemilla japonica, Undaria pinnatifida, Porphyra haitanensis, Ulva prolifera*, and *Ascophyllum nodosum*. These kelp species can be dried and pulverized into a powder for direct compounding, or the kelp (whole plant) can be extracted to provide a nutrient-dense extract, and that extract, when necessary, can be evaporated to a powder to simplify blending with other constituents to obtain a composition in the form of a loose powder.

In various embodiments, a composition for enhancing metabolism comprises at least one extract of an aquatic plant, such as a kelp extract, that is characterized as being rich in fucoxanthin (CAS No. 3351-86-8). Specific powdered kelp extracts may be characterized as being a fucoxanthin extract, or rich in fucoxanthin, such as from brown algae like kelp. Fucoxanthin is a xanthophyll, a type of marine carotenoid found in brown macroalgae like kelp and in golden-brown microalgae. Marine extracts that are rich in fucoxanthin include, but are not limited to, the extracts of the genus *Fucus, Dictyota* or *Laminaria*. Of use herein is the dried fucoxanthin extract of *Laminaria japonica* (extract of the whole brown kelp plant), primarily because of the unexpected synergistic metabolic response when consumed in combination with L-carnitine, L-tyrosine and/or L-cysteine. This extract, labeled as *Laminaria japonica* Aresch extract of the whole brown kelp plant, is available from Naturmed Scientific GMBH, Wiesbaden, Germany or Naturmed Scientific PVT LTD, Delhi, India.

In various embodiments, compositions of the present disclosure comprise *Gynostemma pentaphyllum* (Jiaogulan) plant extract. *Gynostemma pentaphyllum* is an herb that grows wild in Asia. More specifically, *Gynostemma pentaphyllum* is a dioecious, herbaceous climbing vine of the family Cucurbitaceae found widely distributed in South and East Asia as well as in New Guinea. For use in the compositions herein, a *Gynostemma pentaphyllum* leaves and stem extract is used, such as a powdered extract to simplify blending of a powdered composition. A powdered *Gynostemma pentaphyllum* leaves and stem extract is available, for example, from Undersun Biomedtech Corp., Ontario, California 91761. This material, finding use in the metabolism enhancing compositions of the present disclosure, is characterized as a light brown to yellow powder, obtained from a grain alcohol extraction of the leaves and stems, and assigned CAS No. 80321-63-7. The powdered extract is available as standardized 20%, 30%, 40%, 80%, 90% or 98% Gypenosides.

In various embodiments, compositions of the present disclosure comprise a ginger root (*Zingiberaceae*) extract. For use herein, an extract of *Kaempferia parviflora* (black ginger) is chosen, having the very deep purple to nearly black color indicative of large amounts of polymethoxyflavones (PMFs) known to increase energy production by activating AMPK in C2C12 myoblasts. This extract is also available from Naturmed Scientific GMBH, Wiesbaden, Germany or Naturmed Scientific PVT LTD, Delhi, India. For a review of black ginger see, for example, K. Toda, et al., "Black ginger extract increases physical fitness performance and muscular endurance by improving inflammation and energy metabolism," *Heliyon*, 2016 May; 2(5), Article No. e00115.

In various embodiments, compositions of the present disclosure comprise an extract of *Garcinia mangostana*, such as an extract of the mangosteen fruit. This extract is rich in the polyphenolic xanthone α-mangostin. *Garcinia mangostana* fruit extract (CAS No. 90045-25-3) is available, for example, from Naturmed Scientific GMBH, Wiesbaden, Germany or Naturmed Scientific PVT LTD, Delhi, India.

In various embodiments, compositions of the present disclosure comprise an isolated bioactive obtained from a terrestrial or aquatic plant, root, seed, or fruit material. Bioactive substances for use herein include, but are not limited to, alkaloids, anthocyanidins, aurones, chalcones, dihydrochalcones, lignan, peptides, tannins, terpenes, sesquiterpenes, diterpenes, triterpenes, ketones, aldehydes, omega-3-fatty acids, cinnamic acids, benzoic acids, carotenoids, flavones, isoflavones, flavonols, flavanones, isoflavanones, dihydroflavonols, flavans, isoflavnes, flavan-3-ols, flavonoids, dithiolthiones, phytosterols, phytoestrogens, flucosinolates, stilbenoids, and polyphenols.

In various embodiments, a metabolism boosting composition comprises (−)-epigallocatechin gallate, (+)-gallocatechin gallate, (−)-epigallocatechin, lycopene, resveratrol, berberine HCl, carvacrol, cinnamaldehyde, or eugenol, or mixtures thereof as a bioactive. For a review on plant food-derived bioactive compounds see, for example, M. Samitiya, et al., "Potential Health Benefits of Plant Food-Derived Bioactive Components: An Overview," *Foods*, 10(4), 839, 2021.

In various embodiments, a metabolism boosting composition herein comprises berberine, a naturally occurring quaternary ammonium isoquinoline alkaloid with formal name 9,10-dimethoxy-5,6-dihydro-2H-7$\lambda^5$-[1,3]dioxolo[4,5-g]isoquinolino[3,2-a]isoquinolin-7-ylium, and CAS No. 2086-83-1, (typically isolated as its chloride salt denoted as berberine HCl, CAS No. 633-65-8). This compound is isolable from goldenseal, barberry, Oregon grape, yellowroot, Amur cork tree, Chinese goldthread, prickly poppy, California poppy and tree turmeric sources. Berberine HCl is available as a powder having a bulk density of about 15-45 g/100 mL from Parchem Fine & Specialty Chemicals, New Rochelle, NY 10801.

Vitamin, Essential Trace Mineral, or Enzyme or Vitamin Cofactor

In various embodiments, metabolism boosting compositions of the present disclosure comprise at least one vitamin, essential trace mineral, or a cofactor to an enzyme or vitamin, including provitamins.

Vitamins for use herein include any of the known or to be discovered vitamins, such as Vitamin A, B1 (thiamine), B2 (riboflavin), B3 (niacin), B5 (pantothenic acid), B6 (pyridoxine), B7 (D-(+)-biotin), B9 (folic acid), B12 (cyanocobalamin), C, D, E, K and mixtures thereof.

In various embodiments, metabolism boosting compositions of the present disclosure include a vitamin combination consisting of Vitamin C, niacinamide (Vitamin B3), 5-methyltetrahydrofolate (dietary provitamin to Vitamin B9), D-(+)-biotin (Vitamin B7 or "H") and methyl cobalamin (Vitamin B12).

Trace minerals for use in the compositions of the present disclosure include, but are not limited to, calcium, chloride, chromium, cobalt, copper, fluorine, iodine, iron, magnesium, manganese, molybdenum, nickel, phosphorus, potassium, selenium, sodium, sulfur, vanadium, zinc, and mixtures thereof.

In various embodiments, metabolism boosting compositions of the present disclosure include a trace mineral combination consisting of zinc gluconate, selenomethionine (a naturally occurring amino acid, formula $C_5H_{11}NO_2Se$, and a source of dietary selenium), chromium polynicotinate, molybdenum bis-glycinate, and vanadium nicotinate glycinate. This combination provides the trace elements zinc, selenium, chromium, molybdenum, and vanadium to the metabolism boosting composition.

In various embodiments, metabolism boosting compositions of the present disclosure include a vitamin and trace minerals combination consisting essentially of Vitamin C, niacinamide (Vitamin B3), 5-methyltetrahydrofolate (Vitamin B9), D-(+)-biotin (Vitamin B7), zinc gluconate, selenomethionine, chromium polynicotinate, molybdenum bis-glycinate, and vanadium nicotinate glycinate.

Enzyme or vitamin cofactors for use in the compositions of the present disclosure include, but are not limited to, adenosine triphosphate (ATP), S-adenosyl methionine, cytidine triphosphate, glutathione, heme, lipoamide, metanofuran, molybdopterin, 3'-phosphoadenosine-5'-phosphosulfate, methyl cobalamin (provitamin to vitamin B12), deoxyadenosylcobalamin, tetrahydrofolate, coenzyme A, B, M, or Q, thiamine pyrophosphate, flavin mononucleotide, flavin adenine dinucleotide, nicotinamide adenine dinucleotide (NAD+), nicotinamide adenine dinucleotide phosphate (NADP+), pyridoxal phosphate, β-carotene (provitamin to vitamin E), menaquinone, pyrroloquinoline quinone, tetrahydrobiopterin, and tetrahydromethanopterin.

Amino Acids

In various embodiments, a metabolic boosting composition in accordance with the present disclosure comprises at least one amino acid. Amino acids for use herein include, but are not limited to, the amino acids in Table 1, namely, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, the corresponding D-isomer of any of the aforementioned amino acids in Table 1, a homo amino acid, a β-homo amino acid, an N-methyl amino acid, an α-methyl amino acid, or an unusual amino acid, such as for example, citrulline, hydroxyproline, pyrrolysine, norleucine, 3-nitrotyrosine, nitroarginine, ornithine, naphthylalanine, methionine sulfoxide, methionine sulfone, 2-aminohexanedioic acid, 2-aminobutanoic acid, 2-aminodecanoic acid, 2-aminoheptanedioic acid, γ-amino-β-hydroxybenzenepentanoic acid, 2-aminooctanedioic acid, 2-carboxyazetidine, 4-amino-3-hydroxybutanoic acid, γ-amino-β-hydroxycyclohexanepentanoic acid, 3-cyclohexylalanine, 3-sulfoalanine, 2,4-diaminobutanoic acid, diaminopropionic acid, diaminopimelic acid, 2,3-diaminopropanoic acid, 2,7-diaminooctanedioic acid, S-ethylthiocysteine, γ-glutamic acid, γ-carboxyglutamic acid, pyroglutamic acid, 2-hydroxyisovaleric acid, 5-hydroxylysine, 4-hydroxyproline, α-amino-2-indanacetic acid, isovaline, 3-hydroxy-4-methylproline, 3-naphthylalanine, norleucine, N-benzylglycine, nortyrosine, norvaline, 2-carboxyoctahydroindole, N-methylglycine, 4-amino-3-hydroxy-6-methylheptanoic acid, 3-thienylalanine, 3-methylvaline and α-amino-2,4-dioxopyrimidinepropanoic.

In various embodiments, a metabolic boosting composition comprises at least one branched chain amino acid selected from L-valine, L-leucine, and L-isoleucine.

In various embodiments, a metabolic boosting composition comprises a combination of two amino acids selected from the group consisting of L-carnitine, L-tyrosine L-valine, L-leucine, L-isoleucine, and L-cysteine.

In various embodiments, a metabolic boosting composition comprises an amino acid combination consisting essentially of L-cysteine and L-tyrosine.

Antioxidants

In various embodiments, a metabolic boosting composition in accordance with the present disclosure also includes at least one antioxidant. Choices of antioxidant for use in the compositions herein may be made based on Oxygen Radical Absorbance Capacity (ORAC), Total Antioxidant Capacity (TAC) and/or Total Oxyradical Scavenging Capacity (TOSC) scoring. A high ORAC, TAC or TOSC score for a compound indicates high antioxidant capacity. Pertaining to fruits, nuts, and vegetables, TAC levels are affected by a wide array of factors, such as cultivar, growing conditions, harvesting, food processing and preparation, sampling, and analytical procedures. In addition to the ORAC assay, some other measures of TAC include ferric ion reducing antioxidant power (FRAP) and Trolox equivalent antioxidant capacity (TEAC) assays. See, for example, D. P. Tomer, et al., "Comparison of the total oxyradical scavenging capacity and oxygen radical absorbance capacity antioxidant assays," *J. Med. Food,* 10(2), 337-44 (2007), which sets forth the TOSC and ORAC scores for 11 different phytochemicals. For example, although Rutin and α-lipoic acid had low ORAC values, each had high TOSC values when compared to the other phytochemicals, making either of interest in the compositions herein, in addition to other compounds.

Antioxidants for use herein include, but are not limited to, various spices such as cinnamon, peppermint, sorghum, oregano, and turmeric, cocoa, acai berry fruit, β-carotene and other carotenoids in general, glutathione, quercetin, maritime pine bark extract (pycnogenol), grape skin extract, glutathione, coenzyme Q10, α-lipoic acid, various bioflavonoids (eriodyctiol, hesperidin, naringenin), isoflavones (daidzein, genistein, glycitein, biochanin A, formononetin), phenols, polyphenols (e.g., green tea polyphenols), phytoestrogens, selenium, and manganese, (recognizing selenium and manganese are categorized above with the trace minerals).

In various embodiments, a metabolism enhancing composition includes at least one of glutathione, quercetin, α-lipoic acid and pycnogenol as the antioxidant(s).

In various embodiments, a metabolism enhancing composition comprises α-lipoic acid ((R)-5-(1,2-dithiolan-3-yl) pentanoic acid; CAS No. 1200-22-2) as the antioxidant of choice. In various aspects, the racemate may also be used (CAS No. 1077-28-7) rather than the single enantiomer. α-Lipoic acid is a small molecule ($C_8H_{14}O_2S_2$) which is an essential portion of the active sites of enzymes controlling keto-acid oxidation, and which can return Vitamin E and coenzyme C10 back to their reduced states.

Optional Excipient

In various embodiments, a metabolism enhancing composition in accordance with the present disclosure comprises any combination of optional excipients, including functional and non-functional substances as elaborated in the definitions section herein above. In various embodiments, a metabolism enhancing composition contains no excipients. In some instances, there is no taste to mask in a swallowed capsule, and perhaps no need for colorants, sweeteners, or flavoring, and in some instances a dry powdered composition may not require any added preservatives. However, depending on the metabolic composition and the types of botanicals present, a filled capsule designed for extended release or immediate release may benefit from an added flavoring.

In various embodiments, the optional one or more excipients include any one or combination of inert filler, flavoring agent, sweetener, buffer (or individual acidic agent and/or alkali agent), colorant, disintegrant, lubricant or other manufacturing aid, intestinal permeation enhancer, stabilizer, preservative, or other pharmaceutically acceptable substance. Any of these materials not specifically mentioned herein may be found in "Handbook of Pharmaceutical Excipients, 6th Edition, R. C Rowe, et al., editors, Pharmaceutical Press, London, 2009, mentioned above in the context of "excipient." For liquid excipients, or excipients that might be better dispersed if provided in solution, the substance may be sprayed into a ribbon blender with a spray bar as a powdered metabolism boosting composition is blending. In this way, a dry blended powder is still obtained, even though small amounts of liquid ingredients are absorbed in homogeneously. This is the same process as may be used to add liquid plant extracts if the extract is not obtainable as a dry powder.

Suitable flavoring agents can include, for example, natural flavors, artificial flavors, and combinations thereof. Non-limiting examples of flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Suitable flavoring agents also include, for example, artificial, natural and synthetic fruit flavors, such as vanilla, citrus oils (e.g., lemon, orange, lime, and grapefruit), and fruit essences (e.g., apple, pear, peach, grape, strawberry, raspberry, cherry, plum, pineapple, and apricot), and the like, and combinations thereof. Depending on the types and amounts of plant, root, seed and fruit materials and extracts that may be present in a metabolism boosting composition, the composition may already have a certain flavor (and scent), such as driven by ginger or other strongly perceived botanical ingredients.

Other flavoring and fragrant aromatics that may be included individually or in combination include, but are not limited to, anethole, menthol, menthone, menthyl acetate, eucalyptol, borneol, borneol acetate, camphor, 1,8-cineole, cinnamaldehyde, benzaldehyde, citral, thujone, eugenol, limonene, geraniol, citronellol, citronellal, pinene, linalool, thymol, carvone, caryophyllene, linalyl acetate, methyl salicylate, and mixtures thereof. Also, substances that provide scent and flavor include, but are not limited to, 3,3,5-trimethylcyclohexanol, methoxycyclohexanol, benzyl alcohol, anise alcohol, cinnamyl alcohol, β-phenyl ethyl alcohol (2-phenylethanol), cis-3-hexenol, musk xylol, isoeugenol, methyl eugenol, α-amylcinnamic aldehyde, anisaldehyde, n-butyl aldehyde, cumin aldehyde, cyclamen aldehyde, decanal, isobutyl aldehyde, hexyl aldehyde, heptyl aldehyde, n-nonyl aldehyde, nonadienol, hydroxycitronellal, benzaldehyde, methyl nonyl acetaldehyde, dodecanol, α-hexylcinnamic aldehyde, undecenal, heliotropin, vanillin, ethyl vanillin, methyl amyl ketone, methyl β-naphthyl ketone, methyl nonyl ketone, musk ketone, diacetyl, acetyl propionyl, acetyl butyryl, acetophenone, β-methyl acetophenone, ionone, methyl ionone, amyl butyrolactone, diphenyl oxide, methyl phenyl glycidate, γ-nonyl lactone, coumarin, cineole, ethyl methyl phenyl glycidate, methyl formate, isopropyl formate, linalyl formate, ethyl acetate, octyl acetate, methyl acetate, benzyl acetate, butyl propionate, isoamyl acetate, isopropyl isobutyrate, geranyl isovalerate, allyl capronate, butyl heptylate, octyl caprylate octyl, methyl heptynecarboxylate, methine octynecarboxylate, isoacyl caprylate, methyl laurate, ethyl myristate, methyl myristate, ethyl benzoate, benzyl benzoate, methylcarbinylphenyl acetate, isobutyl phenylacetate, methyl cinnamate, cinnamyl cinnamate, ethyl anisate, methyl anthranilate, ethyl pyruvate, ethyl α-butyl butylate, benzyl propionate, butyl acetate, butyl butyrate, p-tert-butylcyclohexyl acetate, cedryl acetate, citronellyl acetate, citronellyl formate, p-cresyl acetate, ethyl butyrate, ethyl caproate, ethyl cinnamate, ethyl phenylacetate, ethylene brassylate, geranyl acetate, geranyl formate, isoamyl salicylate, isoamyl isovalerate, isobornyl acetate, linalyl acetate, methyl anthranilate, methyl dihydrojasmonate, 0-phenylethyl acetate, trichloromethylphenyl carbinyl acetate, terpinyl acetate, vetiveryl acetate, and mixtures thereof.

Suitable sweeteners include nutritive carbohydrates such as sucrose, glucose, fructose, trehalose, galactose, mannitol, sorbitol, and xylitol, and artificial sweeteners such as saccharin, aspartame, acesulfame K, cyclamates, neotame, sucralose, *stevia*, and neohesperidin dihydrochalcone (NHDC).

Suitable buffers may comprise one or more acidifying agents or alkaline agents as necessary to neutralize various co-ingredients, form salts of various co-ingredients, and/or achieve a particular pH target for the composition, such as to adjust the local environment in the GI tract as a dosage form dissolves. For liquid metabolism enhancing compositions, it may be desirable to adjust the pH of the liquid composition. Combinations of various acidifying agents and alkaline agents may be used to create buffering systems that stabilize the desired final pH of the composition. Buffers may be mixed buffers, meaning that the alkaline agent is not necessarily the conjugate base of the acidifying agent.

Exemplary acidifying agents for use in the present compositions include, but are not limited to, organic acids of any molecular weight and mineral acids (inorganic acids), and mixtures thereof. Organic acids may include mono-carboxylic acids, di-carboxylic acids, or tri-carboxylic acids, and may be saturated or may have any degree of unsaturation. For example, organic acids for use in various embodiments of the composition in accordance to the present disclosure may include, but are not limited to, formic acid, carbonic acid, acetic acid, lactic acid, oxalic acid, propionic acid, valeric acid, enanthic acid, pelargonic acid, butyric acid, lauric acid, docosahexaenoic acid, eicosapentaenoic acid, pyruvic acid, acetoacetic acid, benzoic acid, salicylic acid, aldaric acid, fumaric acid, glutaconic acid, traumatic acid, muconic acid, malonic acid, malic acid, succinic acid, glutaric acid, adipic acid, pimelic acid, suberic acid, azelaic acid, abietic acid, pimaric acid, sebacic acid, phthalic acid, isophthalic acid, terephthalic acid, maleic acid, citric acid, and combinations thereof.

Exemplary alkaline materials include any organic amines, $NH_3$, alkali metal or alkaline earth hydroxide, any conjugate bases of any organic acids (e.g., R—$COO^-$), and any of the salts of carbonic acid, phosphoric acid, nitric acid and sulfuric acid, and any mixtures thereof. For example, alkaline materials for use in various embodiments of the composition in accordance with the present disclosure may include, but are not limited to, NaOH, KOH, $NH_3$, sodium acetate, sodium succinate, disodium succinate, monosodium citrate, disodium citrate, trisodium citrate, $NaH_2PO_4$, $Na_2HPO_4$, $Na_3PO_4$, $KH_2PO_4$, $K_2HPO_4$, $K_3PO_4$, $NaHSO_4$, $Na_2SO_4$, $KHSO_4$, $K_2SO_4$, $NaHCO_3$, $Na_2CO_3$, $KHCO_3$, $K_2CO_3$, $NaH_3P_2O_7$, $Na_2H_2P_2O_7$, $Na_3HP_2O_7$, $Na_4P_2O_7$, $KH_3P_2O_7$, $K_2H_2P_2O_7$, $K_3HP_2O_7$, $K_4P_2O_7$, and mixtures thereof. Any of these chemical species may exist as various hydrates when purchased as raw materials for use in the present compositions.

Exemplary colorants include the pharmaceutically acceptable colors used for capsules and tablet dosage forms, such as the U.S. FDA certified colors, dyes and lakes for use in pharmaceutical capsules, tablets and syrups. These acceptable colorants include the inorganic pigments such as titanium dioxide, yellow iron oxide, red iron oxide and black iron oxide, the organic pigments such as D&C Red 36, Red 30 and Red 34, the solvent soluble colors D&C Yellow 11, Yellow 7, Red 27, Red 21, Red 17, Green 6, and Violet 2, and the water soluble colors D&C Green 8, Yellow 10, Yellow 8, Orange 4, Red 22, Red 28, Red 33, Green 5, quinoline yellow, FD&C Yellow 5, Yellow 6, Red 4, Red 40, Red 3, Green 3, Blue 1, Blue 2, and ponceau 4R, carmoisine, amaranth, patent blue V and black PN, and a number of "organic lakes." Colorants can be added to the cellulose batch during the process of making cellulose capsules. Or colorants can be added directly into the composition.

Suitable disintegrants include, but are not limited to, sodium starch glycolate, croscarmellose sodium, microcrystalline cellulose, and polyvinylpyrrolidone (crospovidone). Some substances known to be disintegrants can act as controlled release agents as well, since the swelling of an ingredient can not only break apart other structures but can occlude medicinally active compounds. For a review of disintegrants that may find use in the present compositions, see P. M. Desai, "Review of Disintegrants and the Disintegration Phenomena," J. Pharm. Sci., 105, 2545-2555 (2016).

Suitable lubricants used in the manufacture of capsules include magnesium stearate, calcium stearate and zinc stearate. Notably, some of these manufacturing aids supply trace minerals like calcium, magnesium, and zinc. Any of the other common fatty acids work as lubricants in capsule and tablet manufacturing, including lauric, myristic and palmitic acids and metal salts thereof. Also, fatty acid esters, including glyceride esters and sugar esters find use as manufacturing aids in making solid dosage forms. For a review and a listing of useful substances, see Jinjiang Li, et al., "Lubricants in Pharmaceutical Dosage Forms," Lubricants, 2, 21-43 (2014).

Stabilizers and preservatives are generally more important for liquid compositions rather than dry powder compositions. Such substances to preserve orally administered compositions include the parabens, sorbitol, sodium benzoate, benzoic acid, sorbic acid, potassium sorbate, propionic acid, and combinations thereof. Antioxidants include, but are not limited to, vitamin C, vitamin E, butylated hydroxyanisole (BHA), butylated hydroxytoluene (BHT), and propylgallate. In some instances, the antioxidant, such as vitamin C, will double as a vitamin component and a preservative for the composition. For a review of preservatives in pharmaceuticals see, I. Himoudy, "Preservatives and Their Role in Pharma and Clinical Research," *International Journal of Pharma Sciences and Scientific Research*, 2:4, 134-151 (2016).

The metabolism boosting compositions of the present disclosure may also include surfactants. The use of surfactants in drug products, formulations and in emulsions is well known in the art. Surfactants and their uses are further described in U.S. Pat. No. 6,287,860, which is incorporated herein in its entirety.

Exemplary Compositions, Dosage Forms, and Methods of Administration

Table 2 sets forth general embodiments of metabolism boosting compositions with preferred ranges for each of the constituent groups discussed herein above. The ranges relate to the total weight of the indicated constituent group, based on the total weight of the composition (minus capsule weight).

TABLE 2

Metabolism Enhancing Compositions - Exemplary Ranges

| Constituent Group | Description/Examples | Approx. range |
|---|---|---|
| At least one plant, root, seed, or fruit material, or extract thereof, or bioactive therefrom | Any combination of: dried terrestrial plant, root, seed, or fruit material; terrestrial plant, root, seed, or fruit material extract - dried to powder or added as liquid to a bulk powder blend; dried aquatic plant or aquatic root material; aquatic plant or root material extract - dried to powder or added as liquid to a bulk powder blend; a bioactive substance derived from botanical sources. | 30 wt. % to 50 wt. % |
| At least one vitamin, essential trace mineral, or enzyme or vitamin cofactor | Any combination of: vitamins A, B1 (thiamine), B2 (riboflavin), B3 (niacin), B5 (pantothenic acid), B6 (pyridoxine), B7 (biotin), B9 (folic acid), B12 (cyanocobalamin), C, D, E, K, and mixtures thereof; calcium, chloride, chromium, cobalt, copper, fluorine, iodine, iron, magnesium, manganese, molybdenum, nickel, phosphorus, potassium, selenium, sodium, sulfur, vanadium, and zinc; vitamin or enzyme cofactors; provitamins. | 10 wt. % to 20 wt. % |
| At least one amino acid | Any combination of: common α-amino acids (per Table 1) or any other known or unknown amino acids, in any combination, wherein the one or more amino acids comprise any juxtaposition of the amino and carboxylate moieties, (e.g., α-, β-, γ-, δ-, etc.). | 10 wt. % to 15 wt. % |
| At least one antioxidant | Any combination of: chemical compounds characterizable as antioxidants by Oxygen Radical Absorbance Capacity (ORAC), Total Antioxidant Capacity (TAC) and/or Total Oxyradical Scavenging Capacity (TOSC) score. | 10 wt. % to 15 wt. % |
| Optional excipient | Any combination of: functional and/or non-functional materials including inert filler, flavoring agent, sweetener, buffer, acidic agent, alkaline agent, colorant, disintegrant, lubricant or other manufacturing aid, intestinal permeation enhancer, stabilizer, emulsifier, preservative, or other pharmaceutically acceptable substance. | 25 wt. % to 30 wt. % |

Table 3 sets forth metabolism boosting compositions in accordance with the present disclosure. Each of these compositions are obtained by dry-blending each of the dry ingredients in a V-blender (e.g., MAXIBLEND® lab blender) or other suitable mixer configured for mixing dry ingredients. Any liquid excipients may be sprayed into the blender with a spray nozzle. Each of the exemplary composition in Table 3 appear as loose powders and each were filled into two-piece hard shell capsules at a fill weight of 500 mg as indicated.

modate a 500 mg fill. These capsules have a 21.3 mm locked length. Gelatin capsules can be substituted for cellulose capsules.

The metabolism enhancing compositions of the present disclosure may be administered in several ways depending

TABLE 3

Exemplary Metabolism Enhancing Compositions and Dosages:

| Ingredients (wt. % ranges used) | Compositions | | | | |
| --- | --- | --- | --- | --- | --- |
| | 1 | 2 | 3 | 4 | 5 |
| plant, root, seed, or fruit material, or extract thereof, or bioactive therefrom | | | | | |
| *Laminaria japonica* plant extract[1] | -0- | -0- | 5-10 | 5-10 | 5-10 |
| *Alchemilla japonica* plant extract[1] | 5-10 | -0- | -0- | 5-10 | -0- |
| *Hypericum perforatum L.* extract[2] | -0- | 5-10 | -0- | -0- | 5-10 |
| *Kaempferia parviflora* root extract | 5-10 | -0- | 5-10 | -0- | -0- |
| *Eleutherococcus senticosus* root extract | 5-10 | 5-10 | -0- | -0- | -0- |
| *Gynostemma pentaphyllum* plant extract[3] | -0- | 15-25 | 15-25 | 15-25 | 15-25 |
| *Ginko biloba L.* leaf extract | -0- | 15-25 | -0- | -0- | 15-25 |
| *Punica granatum* seed extract | -0- | -0- | -0- | 2-5 | -0- |
| Carica papaya fruit extract | 2-5 | 2-5 | -0- | -0- | 2-5 |
| *Garcinia mangostana* fruit extract | -0- | -0- | 2-5 | 2-5 | -0- |
| Lycopene | 5-10 | -0- | -0- | -0- | 5-10 |
| Berberine HCl | -0- | -0- | 5-10 | -0- | -0- |
| Resveratrol | 5-10 | 5-10 | -0- | 5-10 | -0- |
| vitamin, essential trace mineral, or enzyme or vitamin cofactor | | | | | |
| Vitamin C | 5-10 | 5-10 | 5-10 | 5-10 | -0- |
| Niacinamide (Vitamin B3) | 0.5-1.5 | 0.5-1.5 | 0.5-1.5 | 0.5-1.5 | 0.5-1.5 |
| L-5-Methyltetrahydrofolate | 0.01-0.05 | 0.01-0.05 | 0.01-0.05 | 0.01-0.05 | 0.01-0.05 |
| D-(+)-Biotin | 0.01-0.05 | 0.01-0.05 | 0.01-0.05 | 0.01-0.05 | 0.01-0.05 |
| Vitamin B12 | 0.01-0.05 | 0.01-0.05 | 0.01-0.05 | 0.01-0.05 | 0.01-0.05 |
| Zinc glycinate | -0- | 1.0-1.5 | 1.0-1.5 | 1.0-1.5 | 1.0-1.5 |
| Selenomethionine | 2-5 | -0- | -0- | 2-5 | 2-5 |
| Chromium polynicotinate | 0.1-0.5 | 0.1-0.5 | 0.1-0.5 | 0.1-0.5 | 0.1-0.5 |
| Molybdenum bis-glycinate | -0- | 0.25-0.5 | 0.25-0.5 | 0.25-0.5 | 0.25-0.5 |
| Vanadium nicotinate glycinate | -0- | 0.5-1.0 | 0.5-1.0 | 0.5-1.0 | 0.5-1.0 |
| Magnesium citrate | 2-5 | -0- | -0- | -0- | 2-5 |
| Calcium citrate | -0- | 2-5 | -0- | 2-5 | -0- |
| amino acids | | | | | |
| L-Carnitine | 5-7.5 | -0- | -0- | -0- | -0- |
| L-Tyrosine | -0- | 5-7.5 | 5-7.5 | -0- | -0- |
| L-Valine | -0- | -0- | -0- | 5-7.5 | -0- |
| L-Leucine | -0- | -0- | -0- | 5-7.5 | 5-7.5 |
| L-Isoleucine | -0- | 5-7.5 | -0- | -0- | -0- |
| L-Cysteine | 5-7.5 | -0- | 5-7.5 | -0- | 5-7.5 |
| Antioxidants | | | | | |
| Glutathione | 5-7.5 | -0- | -0- | -0- | -0- |
| Quercetin | -0- | 5-7.5 | -0- | -0- | -0- |
| α-Lipoic acid | -0- | -0- | 5-7.5 | 5-7.5 | -0- |
| Pycnogenol | -0- | -0- | -0- | -0- | 5-7.5 |
| Excipients[4] | | | | | |
| Excipients[4] | -q.s.- | -q.s.- | -q.s.- | -q.s.- | -q.s.- |
| Total | 100% | 100% | 100% | 100% | 100% |
| Capsule Fill | 500 mg | 500 mg | 500 mg | 500 mg | 500 mg |

TABLE 3 footnotes: (1) dried fucoxanthin extract from the whole kelp plant was used; (2) dried extract of the capsules, flowers, leaves and stem heads of the entire plant was used; (3) dried extract of both leaves and stems of the plant was used; and (4) mixtures of starches, inert filler and processing aids were added as necessary as needed functionally and as "quantity sufficient" to reach 100.0 wt. %. Cellulose capsules were used in these examples and were size 0 (90 mg weight empty, 0.68 mL volume) to accomupon whether local or systemic treatment is desired. Administration may be topical (including ophthalmic and to mucous membranes including vaginal and rectal delivery), pulmonary, e.g., by inhalation or insufflation of powders or aerosols, including by nebulizer; intratracheal, intranasal, epidermal, and transdermal), oral or parenteral. Parenteral administration includes intravenous, intraarterial, subcutaneous, intraperitoneal, or intramuscular injection or infusion; or intracranial, e.g., intrathecal, or intraventricular, administration. Metabolism enhancing compositions for topical administration may include transdermal patches, ointments, lotions, creams, gels, drops, suppositories, sprays, liquids, and powders. Conventional pharmaceutically acceptable carriers, aqueous, powder or oily bases, thickeners, and the like, may be necessary or desirable. In various embodiments, metabolism enhancing compositions comprise loose dry powders that are filled into dissolvable capsules for oral administration and gastrointestinal absorption. Capsules for loose fill of powders are typically cellulose or gelatin.

The metabolism enhancing compositions of the present disclosure, which may conveniently be presented in unit dosage form such as a capsule, may be prepared according to conventional techniques well known in the pharmaceutical industry. Such techniques include the step of bringing into association the active ingredients with any excipient. In general, the metabolism enhancing compositions are prepared by uniformly blending dry ingredients in a suitable mixture such as a ribbon blender.

The metabolism enhancing compositions of the present disclosure may be formulated into any of many possible dosage forms such as, but not limited to, tablets, capsules, gel capsules, liquids, liquid syrups, soft gels, suppositories, and enemas. The compositions of the present disclosure may also be formulated as suspensions in aqueous, non-aqueous or mixed media. Aqueous suspensions may further contain substances which increase the viscosity of the suspension or help to stabilize the suspension.

One of skill in the art will recognize that compositions are routinely designed according to their intended use, i.e., route of administration.

Metabolism enhancing compositions for oral administration include powders or granules, microparticulates, nanoparticulates, capsules, gel capsules, sachets, tablets or minitablets.

Dosage Regimens

In various embodiments of, methods of treating metabolism disorders such as defined under the umbrella metabolic syndrome are described. In general, a method of boosting metabolism in an individual in need thereof comprises orally administering to the individual a therapeutically effective amount of a metabolism enhancing composition comprising in accordance with the present disclosure (such as a composition of Table 3). In various embodiments, the individual in need thereof has been diagnosed as having metabolic syndrome, or individually any one or more of the ailments associated with the syndrome (excess body fat, fatigue, insulin resistance, and so forth).

In various embodiments, a method of enhancing metabolism in an individual in need thereof comprising orally administering to the individual a therapeutically effective amount of a metabolism enhancing composition comprising at least one plant, root, seed, or fruit material, or extract thereof, or bioactive therefrom; at least one vitamin, essential trace mineral, or enzyme or vitamin cofactor; at least one amino acid; at least one antioxidant; and optionally, an excipient. In various embodiments, the metabolism boosting composition is a composition according to Table 2 or Table 3 herein.

Metabolism enhancing compositions of the present disclosure may be delivered orally, in granular form including sprayed dried particles, or complexed to form micro or nanoparticles, which may be administered as a loose powder that can be mixed into a beverage or packed into capsules for swallowing. In various embodiments, the metabolism enhancing compositions are dry blended loose powders, with the dosage form comprising a capsule; and the blended loose powder contained therein.

Capsule dosages are typically set at 500 mg fill per capsule for a dry powdered metabolism boosting composition in accordance with the present disclosure. A therapeutically effective amount is from about one (1) 500 mg capsule to about eight (8) 500 mg capsules orally administered per day for an average weight male or female human individual, equating to about 0.5 to about 4 grams metabolism enhancing composition ingested orally per day. A prophylactically effective amount is from about one (1) 500 mg capsule to about eight (8) 500 mg capsules orally administered per day for an average weight male or female human individual, equating to about 0.5 to about 4 grams metabolism enhancing composition ingested orally per day.

Uses in Medicine

In various embodiments, a metabolism boosting composition in accordance with the present disclosure finds various uses in medicine.

A composition comprising at least one plant, root, seed, or fruit material, or extract thereof, or bioactive therefrom; at least one vitamin, essential trace mineral, or enzyme or vitamin cofactor; at least one amino acid; at least one antioxidant; and optionally, an excipient, for use in the treatment of metabolic syndrome in a subject in need thereof.

A composition comprising at least one plant, root, seed, or fruit material, or extract thereof, or bioactive therefrom; at least one vitamin, essential trace mineral, or enzyme or vitamin cofactor; at least one amino acid; at least one antioxidant; and optionally, an excipient, for use as a medicament in the treatment of metabolic syndrome in a subject in need thereof.

At least one plant, root, seed, or fruit material, or extract thereof, or bioactive therefrom; at least one vitamin, essential trace mineral, or enzyme or vitamin cofactor; at least one amino acid; at least one antioxidant; and optionally, an excipient, for use as a medicament in the treatment of metabolic syndrome in a subject in need thereof.

In the detailed description, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, coupled or the like may include permanent (e.g., integral), removable, temporary, partial, full, and/or any other possible attachment option. Any of the components may be coupled to each other via friction, snap, sleeves, brackets, clips, or other means now known in the art or hereinafter developed. Additionally, any reference to without contact (or similar phrases) may also include reduced contact or minimal contact.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

The invention claimed is:

1. A metabolism enhancing composition consisting essentially of: *Laminaria japonica* fucoxanthin extract of whole kelp, *Gynostemma pentaphyllum* (Jiaogulan) leaves and stem extract, *Kaempferia parviflora* root extract, *Garcinia mangostana* fruit extract, berberine HCl, Vitamin C, Vitamin B3, L-5-methyltetrahydrofolate, Vitamin B7, Vitamin B12, zinc, selenium, chromium, molybdenum, vanadium, L-tyrosine, L-cysteine, and α-lipoic acid.

2. A pharmaceutical dosage form for enhancing metabolism in a subject in need thereof, the pharmaceutical dosage form comprising: a metabolism enhancing composition according to claim 1; and a capsule shell enclosing said composition.

3. The pharmaceutical dosage form of claim 2, wherein each capsule contains approximately 500 mg of said composition.

4. A method of treating metabolic syndrome in an individual in need thereof, the method comprising orally administering 1 to 8 capsules of the pharmaceutical dosage form of claim 3 daily to the individual in need thereof.

* * * * *

UNITED STATES PATENT AND TRADEMARK OFFICE
CERTIFICATE OF CORRECTION

| | |
|---|---|
| PATENT NO. | : 11,878,007 B1 |
| APPLICATION NO. | : 17/818836 |
| DATED | : January 23, 2024 |
| INVENTOR(S) | : Suzanne Bentz |

It is certified that error appears in the above-identified patent and that said Letters Patent is hereby corrected as shown below:

In the Claims

Claim 1, Column 24, Line 16, delete "parvflora" and insert --parviflora--

Signed and Sealed this
Twentieth Day of August, 2024

Katherine Kelly Vidal
*Director of the United States Patent and Trademark Office*